(12) United States Patent  (10) Patent No.: US 8,715,255 B2
Christen et al.  (45) Date of Patent: May 6, 2014

(54) FASTENING DEVICE FOR A DRAINAGE CONTAINER

(75) Inventors: Lukas Christen, Hochdorf (CH); Michael Larsson, Zug (CH)

(73) Assignee: Medela Holding AG, Baar (CH)

( * ) Notice: Subject to any disclaimer, the term of this patent is extended or adjusted under 35 U.S.C. 154(b) by 498 days.

(21) Appl. No.: 12/162,152

(22) PCT Filed: Jan. 12, 2007

(86) PCT No.: PCT/CH2007/000015
§ 371 (c)(1),
(2), (4) Date: Jul. 25, 2008

(87) PCT Pub. No.: WO2007/085100
PCT Pub. Date: Aug. 2, 2007

(65) Prior Publication Data
US 2009/0030384 A1  Jan. 29, 2009

(30) Foreign Application Priority Data

Jan. 27, 2006 (CH) ..................................... 0141/06

(51) Int. Cl.
*A61M 1/00* (2006.01)
*A61G 7/05* (2006.01)
*A61M 5/14* (2006.01)
*F16M 13/02* (2006.01)
*A61J 9/06* (2006.01)

(52) U.S. Cl.
CPC ..... *A61M 1/0001* (2013.01); *A61M 2001/0017* (2013.01); *A61M 2209/082* (2013.01); *A61G 7/0503* (2013.01); *A61M 1/0023* (2013.01); *A61M 5/1414* (2013.01); *A61M 5/1415* (2013.01); *A61M 5/1417* (2013.01); *A61M 2209/08* (2013.01); *A61M 2209/084* (2013.01); *F16M 13/02* (2013.01); *F16M 2200/02* (2013.01); *F16M 2200/027* (2013.01); *A61G 7/05* (2013.01); *A61J 2009/0661* (2013.01)
USPC ............ 604/319; 604/540; 604/317; 604/322

(58) Field of Classification Search
CPC ............ A61M 1/0001; A61M 1/0023; A61M 2001/00; A61M 2001/0001; A61M 2001/0017; A61M 5/1414; A61M 5/1415; A61M 5/1417; A61M 1/0011; A61M 2209/08; A61M 2209/082; A61M 2209/084; F16M 13/00; F16M 13/005; F16M 13/02; F16M 13/022; F16M 2200/02; F16M 2200/027; F16M 2200/028; A61G 7/05; A61G 7/0503; A61G 7/0507; A61G 13/101; A61G 13/102; A61J 2009/0661; A61J 2009/0684
USPC ............ 604/319, 322, 541, 543; 220/495.01, 220/495.06; 248/226.11, 220.21, 220.22, 248/221.11, 222.11, 222.13, 223.41
See application file for complete search history.

(56) References Cited

U.S. PATENT DOCUMENTS

| | | | |
|---|---|---|---|
| 3,680,560 A | | 8/1972 | Pannier, Jr. et al. |
| 3,915,189 A | | 10/1975 | Holbrook et al. |
| 3,955,572 A | | 5/1976 | Martin |
| 4,088,250 A | * | 5/1978 | Schaefer ...................... 224/235 |
| 4,101,043 A | | 7/1978 | Johnson, Jr. et al. |
| 4,111,204 A | * | 9/1978 | Hessel ........................ 604/321 |
| 4,307,864 A | * | 12/1981 | Benoit ...................... 248/222.11 |
| 4,397,643 A | * | 8/1983 | Rygiel ........................ 604/317 |
| 4,419,093 A | | 12/1983 | Deaton |
| 4,516,973 A | * | 5/1985 | Telang ........................ 604/319 |
| 4,795,448 A | * | 1/1989 | Stacey et al. .................. 604/319 |
| 4,844,397 A | * | 7/1989 | Skakoon et al. ......... 248/231.71 |
| 4,926,722 A | * | 5/1990 | Sorensen et al. ................ 81/487 |
| 5,035,389 A | * | 7/1991 | Wang ...................... 248/224.51 |
| 5,282,783 A | * | 2/1994 | Lindsay ...................... 604/6.09 |
| 5,304,164 A | * | 4/1994 | Lindsay ...................... 604/403 |
| 5,322,253 A | * | 6/1994 | Stevens .................... 248/229.15 |
| 5,356,038 A | | 10/1994 | Banks |
| 5,356,105 A | * | 10/1994 | Andrews .................. 248/221.11 |
| 5,382,244 A | * | 1/1995 | Telang .......................... 604/319 |
| 5,385,324 A | * | 1/1995 | Pryor et al. ................. 248/228.3 |
| 5,437,836 A | * | 8/1995 | Yamada ........................... 422/1 |
| 5,470,324 A | | 11/1995 | Cook et al. |
| 5,637,104 A | | 6/1997 | Ball et al. |

| | | | | |
|---|---|---|---|---|
| 5,730,406 A * | 3/1998 | Chen | | 248/223.41 |
| 5,792,126 A | 8/1998 | Tribastone et al. | | |
| 5,839,603 A * | 11/1998 | Smith et al. | | 220/782 |
| 6,152,902 A * | 11/2000 | Christian et al. | | 604/320 |
| 6,183,453 B1 * | 2/2001 | Swisher | | 604/319 |
| 6,244,759 B1 * | 6/2001 | Russo | | 396/428 |
| 6,290,684 B1 | 9/2001 | Herrick | | |
| 6,315,182 B1 * | 11/2001 | Chen | | 224/420 |
| 6,390,427 B1 * | 5/2002 | McConnell et al. | | 248/231.61 |
| 6,425,349 B1 * | 7/2002 | Laskin et al. | | 119/496 |
| 6,488,675 B1 | 12/2002 | Radford et al. | | |
| 6,494,869 B1 | 12/2002 | Hand et al. | | |
| 6,558,341 B1 * | 5/2003 | Swisher | | 604/6.09 |
| 6,637,707 B1 | 10/2003 | Gates et al. | | |
| 6,733,481 B2 * | 5/2004 | Ow | | 604/317 |
| 7,077,302 B2 * | 7/2006 | Chuang | | 224/420 |
| 7,674,248 B2 * | 3/2010 | Anderson et al. | | 604/319 |
| 2002/0111592 A1 | 8/2002 | Bemis et al. | | |
| 2005/0012017 A1 * | 1/2005 | Ward et al. | | 248/466 |
| 2007/0045493 A1 * | 3/2007 | Somji | | 248/229.14 |

FOREIGN PATENT DOCUMENTS

| | | |
|---|---|---|
| DE | 19913711 | 4/2001 |
| EP | 0092313 A2 | 10/1983 |
| EP | 0861668 A1 | 9/1998 |
| GB | 2086466 | 5/1982 |
| GB | 2333459 A | 7/1999 |
| JP | 2000 079162 A | 3/2000 |
| WO | 83/01767 A1 | 5/1983 |
| WO | 93/18803 A1 | 9/1993 |
| WO | 94/14045 | 6/1994 |
| WO | 96/34636 A1 | 11/1996 |
| WO | 01/49344 A1 | 7/2001 |

OTHER PUBLICATIONS

International Search Report for corresponding International Application No. PCT/CH2007/000015, dated Jul. 31, 2007.

Swiss Search Report for corresponding Swiss Patent Application No. 0141/06, dated Feb. 7, 2006.

German brochure S31 GIK published by Serres Oy and Intersurgical GmbH: Befestigung und Adaption, created in Jun. 2005 and printed. (see the mark S31GIK / 0605 MADHOUSE / I-Print Oy in the right margin of the brochure, 06 = Jun. 5, 2005).

Coopdech FitFix, a brochure of Daiken Medical printed from Internet and having contents as of Nov. 2005.

German brochure S31GII published by Serres Oy and Intersurgical GmbH: AbsaugSystem, created in Jun. 2005 and printed (see the mark S31 Gil / 0605 MADHOUSE / 1-Print Oy in the right margin of the brochure, 06 = Jun. 5, 2005).

www.daiken-iki.co.jp/en/pi/in_ff.html, Coopdech FitFix, retrieved from the Internet Jan. 3, 2013.

Opposition of European patent EP 1976576 filed Jan. 17, 2013 (15 pages).

MEDELA leaflet entitled "Accessories" available at least as of 2005.

* cited by examiner

*Primary Examiner* — Adam Marcetich

(74) *Attorney, Agent, or Firm* — McDonnell Boehnen Hulbert & Berghoff LLP

(57) ABSTRACT

A fastening device for fastening an outer container (1) of a drainage container comprises a snap lock (12). Said snap lock (12) has a slot/slot pin connection (42, 13). A leaf spring (12) having a projecting nose (12') is arranged at a lower end of the connection and engages behind a lower edge of the slot (42) or the slot pin (13). The fastening device according to the invention allows the drainage bag to be replaced in a simple and reliable manner. The corresponding drainage container is inexpensive to produce and allows a reliable operation.

12 Claims, 4 Drawing Sheets

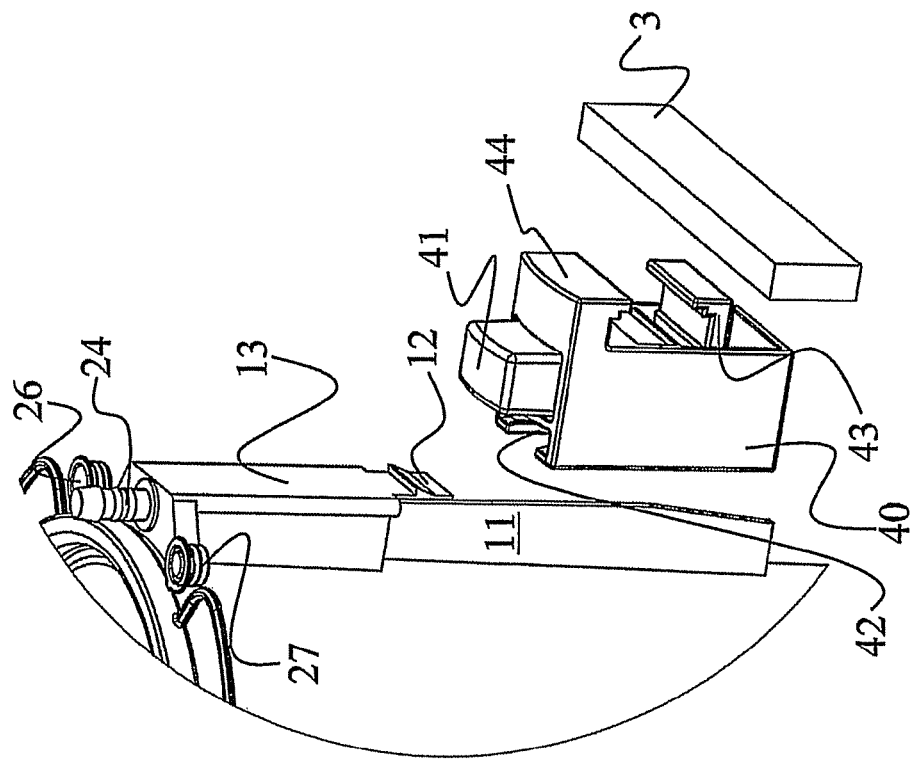
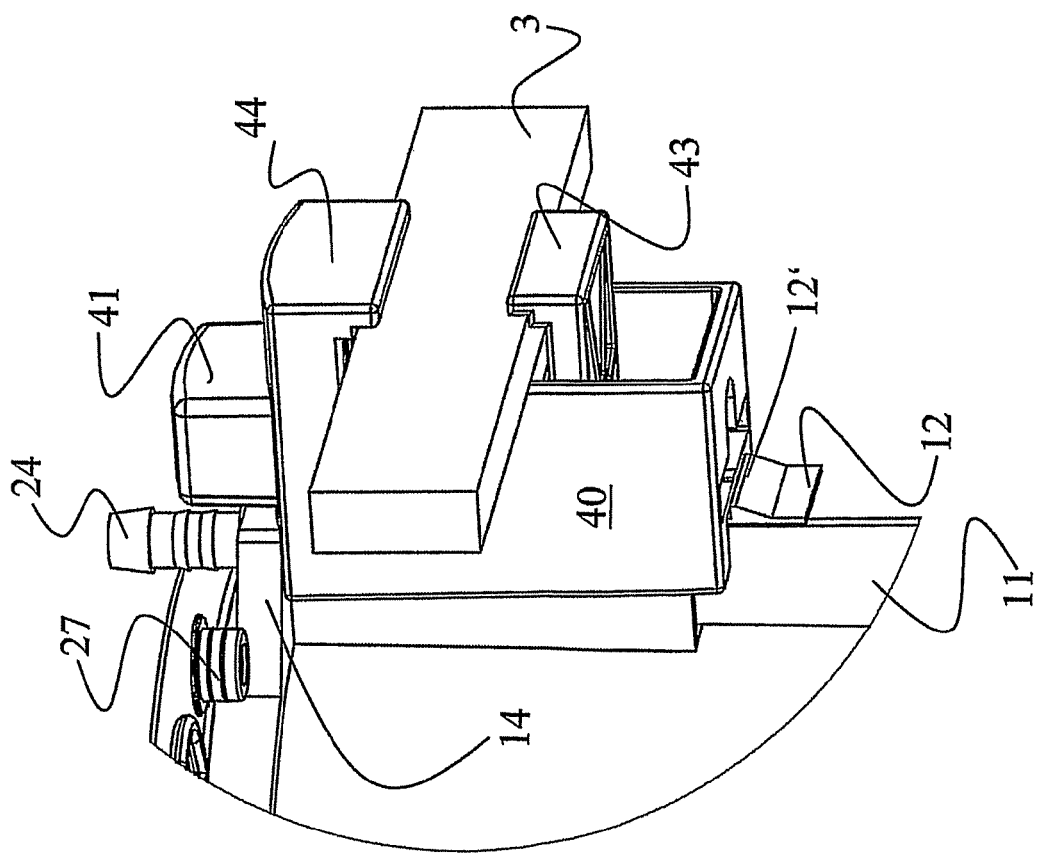
Fig.4
Fig.5

FASTENING DEVICE FOR A DRAINAGE CONTAINER

TECHNICAL FIELD

The invention relates to a fastening device for fastening a drainage container and to a drainage container.

PRIOR ART

Drainage containers are containers for collecting body fluids which are obtained during extraction by suction within medical treatments. The body fluid is led into the container via a patient-side drainage line by means of a vacuum pump. The container has for this purpose a connection for the patient-side drainage line and a connection for the suction or vacuum pump or for the central vacuum.

Drainage containers having a rigid outer container, a lid which closes the outer container and has the above-mentioned connections, and a drainage or collection bag which can be attached or is attached to the lid, are known. The outer container is in this case reusable, the drainage bag is used once and then disposed of appropriately or first washed and only then disposed of. A drainage container of this type is known for example from EP 0 861 668. Further drainage containers are described in U.S. Pat. No. 3,680,560, WO 94/14045 and U.S. Pat. No. 5,470,324.

These drainage containers are conventionally suspended from a rail which is either attached to the patient's bed itself, is arranged on a movable mount or extends along a wall adjacent thereto. The devices that can be used for fastening drainage containers are for example fastening clamps which clamp the rail. As the rails are conventionally of a standard size, the same size of fastening clamps can be used in different hospitals. The drainage container is in this case suspended from the fastening clamp. The fastening clamp thus ensures that the container is held securely during drainage.

Replacing a full drainage bag with an empty one requires both hands, as firstly the container has to be secured and secondly the lid closures released, and the bag has to be lifted out with the lid.

SUMMARY OF THE INVENTION

It is therefore an object of the invention to provide a device allowing drainage bags to be replaced in a simple and reliable manner.

This object is achieved by a fastening device for fastening an outer container of a drainage container.

The fastening device according to the invention for fastening the outer container of the drainage container has a snap lock comprising a snap element. The snap element is preferably a leaf spring having a projecting nose.

The snap lock allows the outer container to be held in its fastened position even when the lid is removed with the drainage bag. The drainage bag can thus be removed rapidly and reliably with one hand without the entire arrangement around it, particularly the outer container, having to be secured by hand.

The snap lock allows the drainage container still to be fastened in a simple manner. Fastening is above all facilitated if the fastening device has a slot/slot pin connection so that, for fastening the drainage container, the slot pin merely has to be inserted into the slot until the snap lock engages.

Preferably, the slot or the slot pin is arranged in a fastening clamp. This fastening clamp can be fastened to a rail. The clamp allows rapid and reliable connection to a rail.

It is advantageous that known fastening clamps can continue to be used and that merely the outer container of the drainage container has to be newly provided with a snap lock. If the snap lock is a leaf spring, the changeover from previous product lines to the drainage container according to the invention is relatively simple and therefore cost-effective.

Obviously, however, the fastening clamp can also be provided with the snap element or have the slot pin.

It is a further object of the invention to provide a drainage container which can be manufactured relatively cost-effectively.

The drainage container according to the invention has a lid which is fastened to the rigid outer container exclusively by resting thereon. It has been found that the lateral clamps used hitherto are not necessary for fastening the lid. The reduced pressure generated in the outer container during drainage is sufficient to hold the lid and thus the drainage bag securely in its position. As this requires the manufacture and assembly of fewer parts, the drainage container can be manufactured more cost-effectively.

Preferably, the lid is provided with handles to allow the lid to be lifted more easily with the drainage bag. As, in the case of a lid made of plastics material, the handles can be extruded jointly with the remainder of the lid, manufacturing costs can be kept low. Two handles, which are formed integrally with or attached to the lid laterally and on two diametrically opposing sides, are preferably provided.

Preferably, the bag is fixedly connected, in particular welded or bonded, to the lid. A separate head part for the bag may thus be dispensed with. This also lowers the manufacturing costs.

It is a further object of the invention to provide a drainage container allowing reliable operation.

This object is achieved by a drainage bag.

The drainage bag according to the invention has in the lid a connection element for the patient-side drainage line, which connection element forms an angle. The angle is preferably approximately 45°. Either the connection fitting itself can be bent or a bent connection pipe can be inserted therein.

The angle eliminates the risk of the patient-side drainage tube becoming kinked, thus restricting the suction effect. Whether the drainage container is arranged at a specific height with respect to the patient is no longer so critical. Within a reasonable range, it is now entirely possible for the drainage container to be located higher or lower than this optimum position.

Further advantageous embodiments emerge from the dependent claims.

BRIEF DESCRIPTION OF THE DRAWINGS

The subject matter of the invention will be described hereinafter based on a preferred exemplary embodiment illustrated in the appended drawing, in which:

FIG. 4 is an enlarged perspective view, compared to FIG. 1, of the fastening device according to the invention;

FIG. 5 shows the fastening device according to FIG. 4 in a released state; and

WAYS OF CARRYING OUT THE INVENTION

Figure 1:
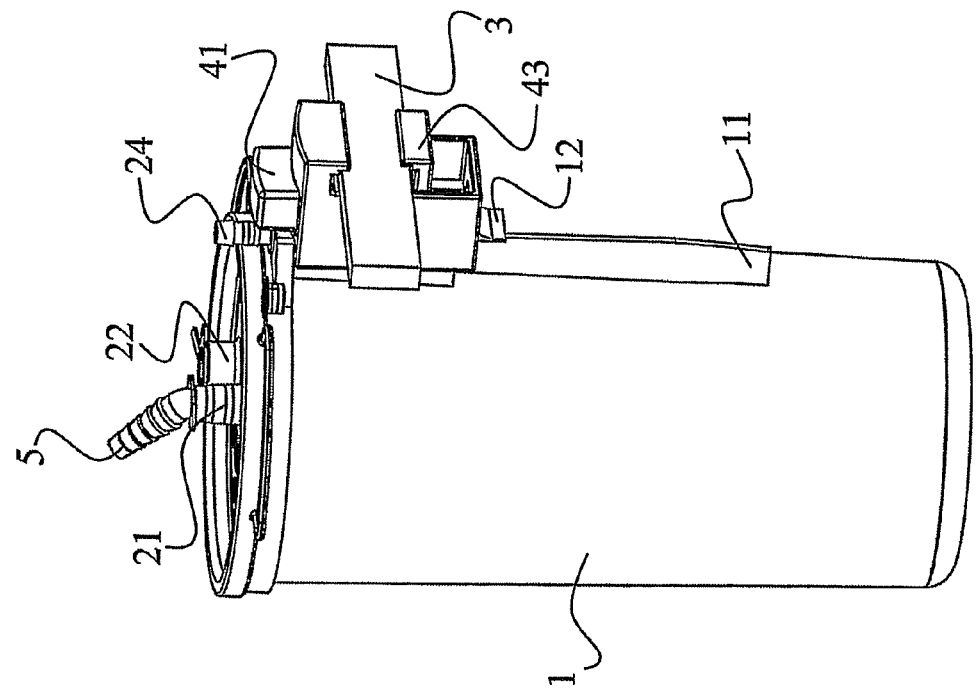
FIG. 1 is a perspective view from a first side of a drainage container according to the invention.
Figure 2:
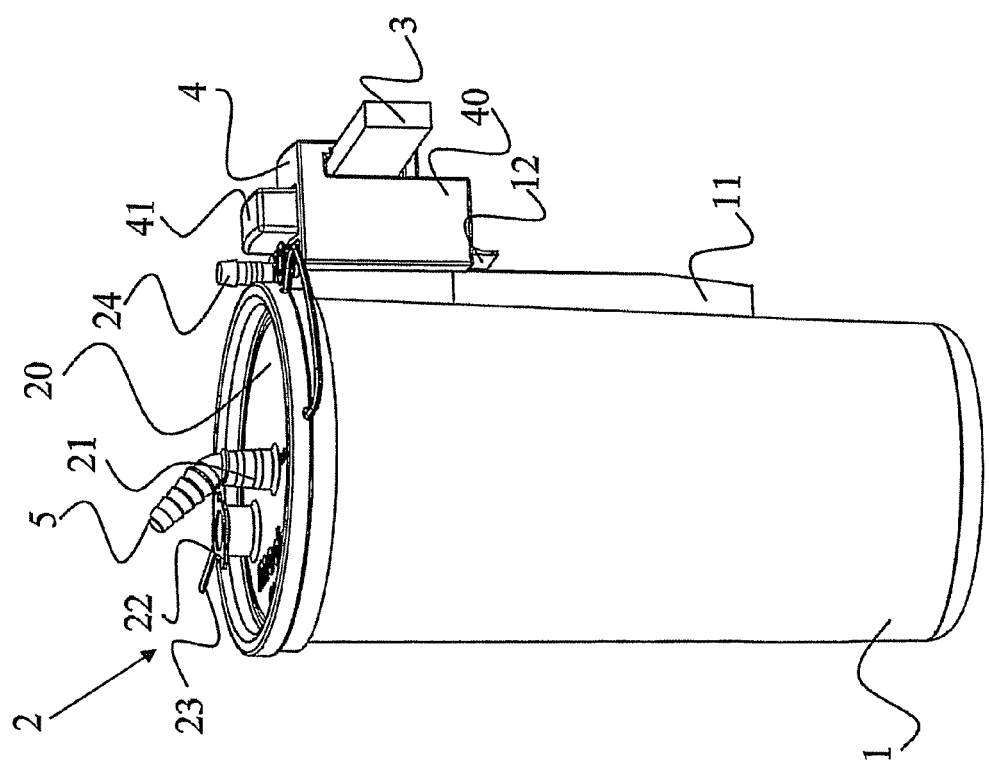
FIG. 2 is a perspective view from a second side of the container according to FIG. 1.
Figure 3:
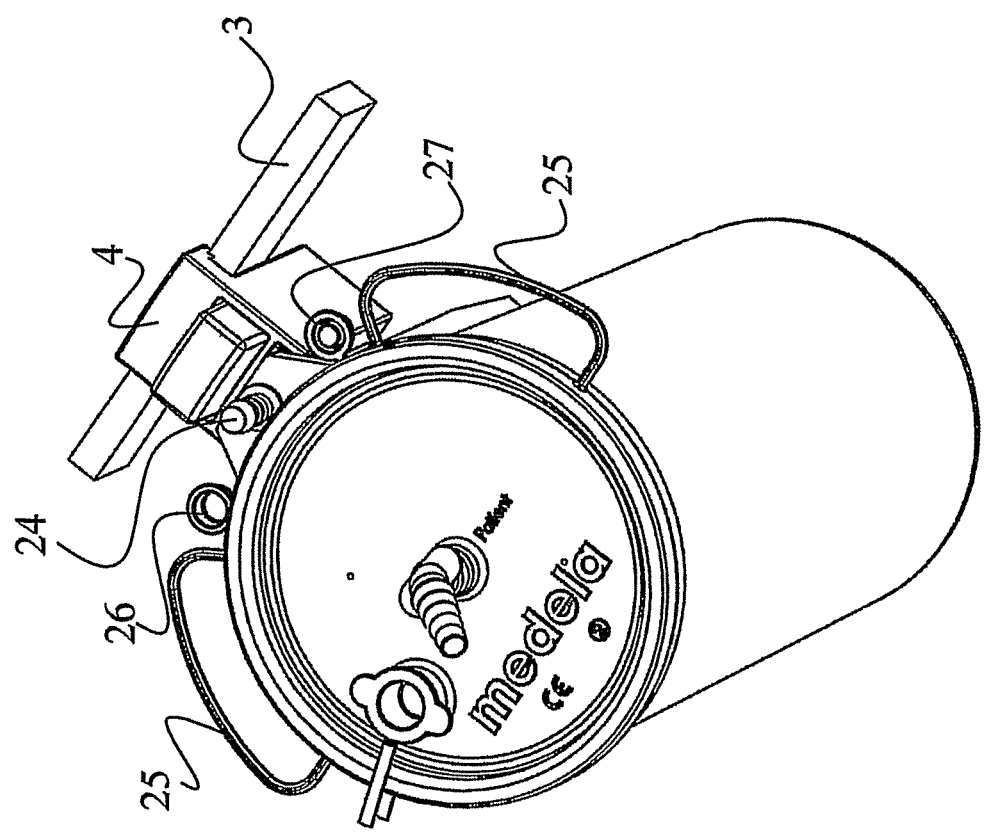
FIG. 3 is a perspective view from a direction from above of the container according to FIG. 1.

FIGS. 1 to 3 are two side views and a view from an upper direction of a drainage container according to the invention. The drainage container has a rigid, preferably transparent outer container 1 and a closure lid 2. A drainage bag (which cannot be seen in the drawings) can be fastened to the lid 2 or it is preferably fixedly connected to the lid 2, for example welded onto or bonded to the circumferential edge thereof. The drainage bag is arranged in the container 1 and is held in its position by the lid 2 resting on the edge of the container. The lid 2, bag and outer container 1 are preferably made of plastics material, wherein the lid and the outer container can be made, for example, of PC (polycarbonate) or PSU (polysulfone) and the bag of PE (polyethylene).

A plurality of openings are provided in the lid 2 or in the circular base 20 thereof. An opening is surrounded by a patient-side connection fitting 21 to which a patient-side drainage line can be connected. This connection fitting 21 forms an opening into the drainage bag. A vacuum connection for connecting to the vacuum source is denoted in the figures by reference numeral 24. In the illustrated exemplary embodiment, this connection is located in a web 11 arranged laterally on the container 1, the opening leading into the interior of the container. It is however also possible to arrange this vacuum connection 24 in the lid.

A connection pipe 5 which forms an angle is inserted into the opening in the connection fitting 21. Preferably, the angle is approximately 45°. The patient-side drainage line is connected to this connection pipe 5. Connection fittings and connection pipes can also be manufactured jointly in one piece.

Further openings or connection fittings may also be provided. In the example illustrated in the present case, a series connection 22 is arranged in the lid 2. The series connection serves to connect two or more drainage containers in series. In this case, the individual containers are joined together by connecting lines which are inserted into these series connections 22. If only a single drainage container is used, the series connection is closed by a lid 23 as shown, thus allowing the necessary vacuum to be generated inside the container. Preferably, the lid 23 of the series connection 22 is formed integrally with the remainder of the lid 2 or otherwise connected thereto.

Handles 25 are formed integrally with or attached to the lid 2. Preferably, the lids and handles are formed jointly in one piece. These handles 25 can protrude upward. However, in the preferred embodiment illustrated in the present case, precisely two handles 25 are provided and arranged on diametrically opposing sides of the lid 2, on the circumferential edge thereof. In this case, they form a common plane with the remainder of the lid.

The lid 2 is not specially fastened to the outer container 1. In particular, no clamps are provided for fastening it. The lid 2 rests merely on the upper edge of the outer container 1 and is held in its position merely by the reduced pressure prevailing in the container during use.

As may be seen most clearly in FIG. 3, two caps 26, 27 are formed integrally with the lid. These caps 26, 27 may be broken off from the remainder of the lid during use and used as closures for the connection fitting 21 and the vacuum connection 24. It is however also possible to attach no cap or only one cap. Furthermore, one cap can be configured so as to be able to be used to close various openings. For example, it can in one position close the connection fitting 21 and be shaped so as to be able in a rotated position to close the vacuum connection 24 or the series connection 22.

The outer container 1 is preferably circularly cylindrical in shape. The aforementioned web 11 is welded onto or formed integrally with the casing of the outer container 1. The web protrudes outward and merges in the upper region with a slot pin 13, as is shown in FIG. 5. The slot pin 13 has a longitudinal direction running parallel to a longitudinal axis of the container 1.

The counterpart to the slot pin 13 is formed by a slot 42 running in a fastening element or a fastening clamp 4. This fastening element 4 can be fastened to a rail of a patient's bed, to a rail of a drainage device, to a wall rail or to another suitable extending rail. The figures show merely a short portion of the rail.

The fastening device according to the invention may now be seen most clearly in FIGS. 4 and 5. The associated fastening element 4 has a basic body 40. On one side of the basic body 40, the aforementioned slot 42 runs in a perpendicular direction. The other side forms the clamp. The upper part of the clamp is in this case a fixed component of the basic body 40 and is formed by a downwardly bent fixed claw 44. The lower part of the clamp is an upwardly bent lower, movable claw 43 which is displaceable in the vertical direction with spring loading. The spring runs inside the basic body 40 and can therefore not be seen in this case. The movable claw 43 is connected to an actuating button, in this case a push-button 41, which protrudes above the upper side of the basic body 40 and can be pressed downward. As a result, it moves the claw 43 downward counter to the spring force. The claw 43 and the downwardly bent upper fixed claw 44 together form a slot which runs in the horizontal direction and in which the rail 3 is received. Obviously, it is also possible for the upper claw to be configured so as to be movable and the lower claw fixed.

The fastening device according to the invention comprises a snap lock 12 formed in this case by a leaf spring 12 having a nose 12' projecting from the upper side of the slot pin 13. The leaf spring 12 is the downwardly directed extension of the slot pin 13, the leaf spring being configured so as to be narrower than the greater width of the slot pin 13. The leaf spring 12 can be made of metal or plastics material or another suitable material. The snap lock can also be configured differently to the manner described in the present document. What is important is that it locks securely as a result of snapping shut, i.e. fixes the outer container to the fastening clamp releasably but securely.

As may be seen in FIG. 5, the fastening clamp 4 is fastened to the rail 3 and the container 1 is inserted with its slot pin 13 from above into the slot 42 in the fastening clamp 4 until it rests with a plate 14 attached to the upper end of the slot pin 13 on the basic body 40. In this position, the snap lock is snapped shut and the projecting nose 121 of the leaf spring 12 engages behind the slot 42 of the fastening element 4. To allow the container 1 to be removed again, the spring 12 must be pressed manually in the direction of the container 1, thus allowing the slot pin 13 to be drawn back upward out of the slot 42. The snap lock thus arrests the container and prevents undesirable tensile movements upward.

Figure 6:
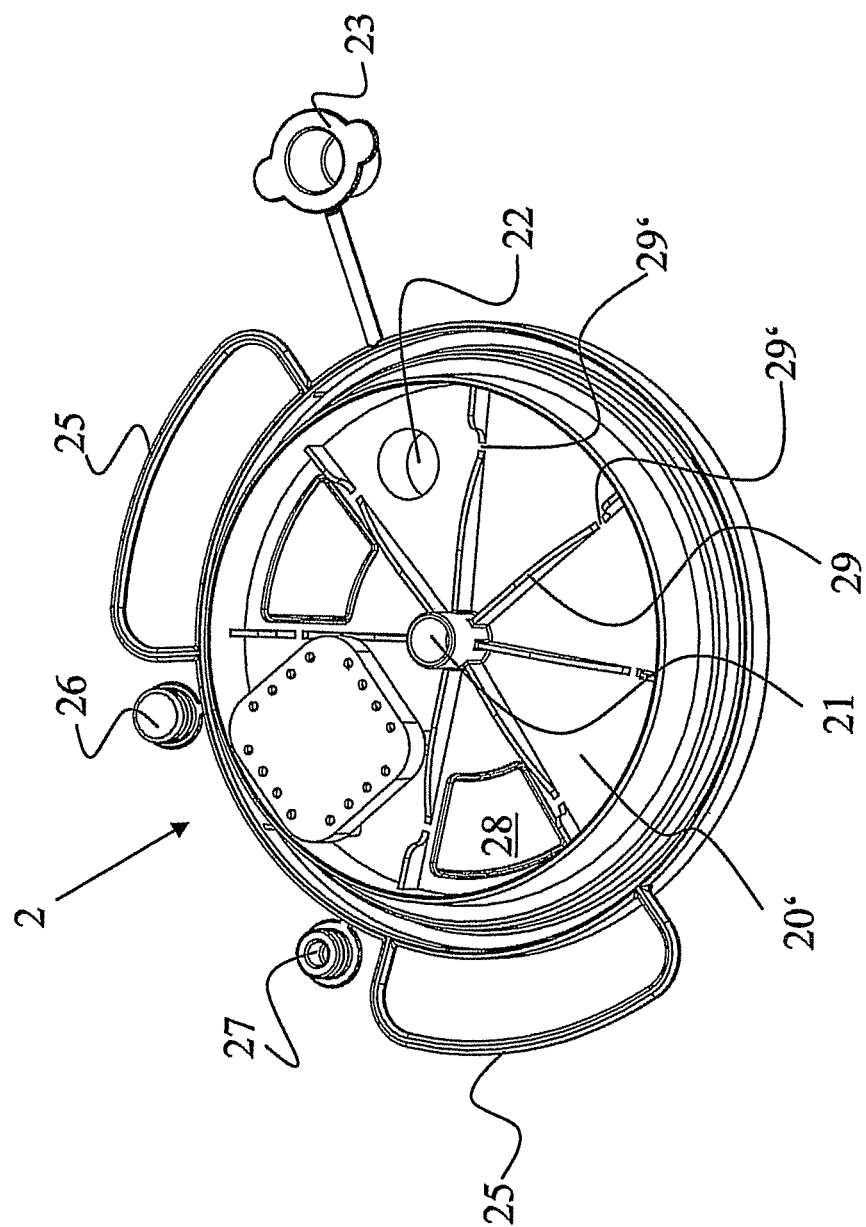
FIG. 6 is a perspective view looking onto the underside of a lid according to the invention.

The lid 2, such as it is shown in FIG. 6, will be explained hereinafter in greater detail. It has on its underside, i.e. the side directed toward the interior of the container, ribs 29 which are arranged in a star-shaped manner and preferably extend almost up to the edge of the lid. Each rib 29 is provided in each case with at least one break 29', so that the individual regions 20' of the inner surface of the lid are joined together. It is thus impossible for any liquid to remain trapped during cleaning of the lid 2.

In order to facilitate cleaning, the lid 2 has at least one region 28, preferably a plurality of regions 28, which can be broken out and by means of which the drainage bag can be emptied rapidly. In the present case, there are two such regions 28. In order to allow the bag and the lid 2 to be washed for the purpose of secure disposal in a washing machine suitable for this purpose, positioning aids (not shown in the present document) are provided, thus allowing the lid 2 to be held at all times in the same position and above all securely in the washing machine. The positioning aid used is preferably at least one hole arranged in a circumferential edge of the lid 2.

The fastening device according to the invention allows simple and reliable replacement of the drainage bag. The associated drainage container can be manufactured cost-effectively and allows reliable operation.

LIST OF REFERENCE NUMERALS

1 Outer container
11 Web
12 Leaf spring
12' Projecting nose
13 Slot pin
14 Plate
2 Closure lid
20 Base
20' Region
21 Patient-side connection fitting
22 Series connection
23 Lid of the series connection
24 Vacuum connection
25 Handle
26 First cap
27 Second cap
28 Region which can be broken out
29 Rib
29' Break
3 Rail
4 Fastening clamp
40 Basic body
41 Push-button
42 Slot
43 Movable claw
44 Fixed claw
5 Connection pipe

The invention claimed is:

1. A drainage container for collecting body fluids extracted by suction, with a fastening device for fastening the drainage container to a rail so that the drainage container is suspended from the rail, wherein the drainage container has:
    a rigid outer container,
    a lid sealingly closing the outer container, and
    a drainage bag for receiving the body fluids, wherein the fastening device comprises a fastening clamp with a basic body, the basic body having a push-button on one side, a spring-loaded movable claw connected to the push-button, and a fixed claw, the spring-loaded movable claw and the fixed claw forming a slot for receiving the rail, wherein the push-button can be pressed in one direction to move the spring-loaded movable claw in the same direction, wherein moving the spring-loaded movable claw releases the rail,
    wherein the fastening device further has a connection comprising a slot and a slot pin, the slot being arranged on an opposite side of the basic body and the slot pin being arranged on the outer container or vice versa,
    wherein the fastening device further comprises a snap lock, a part of the snap lock being arranged on the outer container, the snap lock comprising a leaf spring having a projecting nose, wherein the projecting nose is arranged at a lower end of the connection and engages behind a lower edge of the slot or of the slot pin, and wherein the leaf spring protrudes beyond the lower end of the basic body in the fastened state,
    wherein the drainage bag can be attached or is attached to the lid in such a way that the lid can be removed from the outer container along with the attached drainage bag by a user releasing and lifting the lid from the outer container, and wherein the snap lock holds the outer container fastened to the rail when the lid with the drainage bag is removed, enabling the user to separate the lid and the drainage bag from the outer container with one hand after a drainage is performed; and
    wherein the leaf spring can be pressed manually to allow the slot pin to be drawn back out of the slot, thereby releasing the outer container from the fastening clamp.

2. The drainage container as claimed in claim 1, wherein the movable claw is movable in a direction parallel to a longitudinal direction of the slot or the slot pin.

3. The drainage container as claimed in claim 1, wherein the leaf spring is arranged on the outer container.

4. An outer container of a drainage container as claimed in claim 1, wherein the outer container is rigid,
    the outer container has a casing onto which there is welded or integrally with which there is formed a web which protrudes outward and merges in the upper region with the slot pin,
    the slot pin has a longitudinal direction running parallel to a longitudinal axis of the outer container,
    wherein the leaf spring forms a downwardly directed extension of the slot pin and the projecting nose projects from the upper side of the slot pin, the leaf spring being part of the snap-lock for fastening the outer container to the rail.

5. The drainage container of claim 1 wherein the drainage container has a vacuum connection for connecting to a suction source and a connection fitting for connecting to a patient-side drainage tube, wherein the lid is sealingly fastened to the rigid outer container exclusively by resting thereon.

6. The drainage container as claimed in claim 5, wherein the lid has at least one handle.

7. The drainage container as claimed in claim 6, wherein the at least one handle is arranged on a circumferential edge of the lid and forms a common plane with the lid.

8. The drainage container as claimed in claim 5, wherein the lid has, on an inner surface, ribs arranged in a star-shaped manner and each rib has at least one break, so that regions are formed on the inner surface that are joined together.

9. The drainage container as claimed in claim 5, wherein the lid has at least one region which can be broken out.

10. The drainage container as claimed in claim 9, wherein a positioning aid in the form of at least one hole is provided to position the lid in a washing machine.

11. The drainage container of claim 1 wherein the drainage container has a vacuum connection for connecting to a suction source and a connection fitting for connecting to a patient-side drainage tube, wherein the lid is sealingly fastened to the rigid outer container by a vacuum.

12. The drainage container of claim 1 wherein the outer container comprises a web which protrudes outwardly and wherein the part of the snap lock which is arranged on the outer container is arranged on the web.

* * * * *